United States Patent
Raabe et al.

[11] 4,018,778
[45] * Apr. 19, 1977

[54] DERIVATIVES OF 1-PHENOXY-3-AMINO-PROPANE-2-OL AND PROCESS FOR THEIR PRODUCTION

[75] Inventors: Thomas Raabe, Heusenstamm; Josef Scholtholt, Frankfurt am Main; Rolf-Eberhard Nitz, Bergen-Enkheim, all of Germany

[73] Assignee: Cassella Farbwerke Mainkur Aktiengesellschaft, Frankfurt am Main-Fechenheim, Germany

[ * ] Notice: The portion of the term of this patent subsequent to Aug. 20, 1991, has been disclaimed.

[22] Filed: July 12, 1974

[21] Appl. No.: 488,194

Related U.S. Application Data

[63] Continuation-in-part of Ser. No. 362,567, May 22, 1973, abandoned.

[30] Foreign Application Priority Data

May 24, 1972 Luxembourg ............. 65414

[52] U.S. Cl. .............. 260/296 AE; 424/263; 260/240 J; 260/294.8 R; 260/295 AM; 260/295.5 A; 260/297 R; 260/307 F; 260/348 R; 260/570.5 C; 260/590 C; 260/590 D; 260/590 E; 260/590 R
[51] Int. Cl.² ..................... C07D 213/28
[58] Field of Search ..... 260/296 AE, 240 J, 296 R, 260/295 AM, 295.5 A

[56] References Cited
UNITED STATES PATENTS

| 3,328,417 | 6/1967 | McLoughlin et al. | 260/307 |
|---|---|---|---|
| 3,412,154 | 11/1968 | Fleming et al. | 260/570.5 |
| 3,679,693 | 7/1972 | Ross et al. | 260/296 AE |
| 3,723,476 | 3/1973 | Nakanishi et al. | 260/347.7 |
| 3,830,806 | 8/1974 | Raabe et al. | 260/240 J |
| 3,862,953 | 1/1975 | Berger et al. | 260/295 T |

*Primary Examiner*—John D. Randolph
*Attorney, Agent, or Firm*—Francis M. Crawford

[57] ABSTRACT

The present invention relates to pharmacologically valuable new derivatives of 1-phenoxy-3-amino-propane-2-ol and process for their production. The new derivatives of 1-phenoxy-3-amino-propane-2-ol are suitable for the treatment and prophylaxis of diseases of the heart. Some possess pronounced β-adrenalytic or anti-arythmic properties. These new derivatives have the structural formula

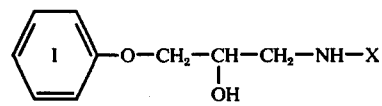

wherein X signifies

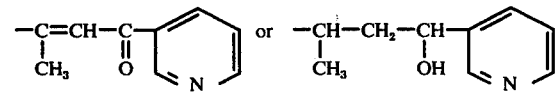

and the phenyl nucleus I may be mono-, di- or trisubstituted by alkyl, alkenyl, alkinyl, cycloalkyl, cycloalkenyl, alkoxy, alkenyloxy, phenyl, halogen or the radical $-NR_1R_2$, in which $R_1$ stands for alkyl or acyl and $R_2$ for hydrogen or alkyl, together with their aldehyde condensation products and their acid addition salts.

13 Claims, No Drawings

DERIVATIVES OF 1-PHENOXY-3-AMINO-PROPANE-2-OL AND PROCESS FOR THEIR PRODUCTION

This application is a continuation-in-part of application Ser. No. 362,567, filed May 22, 1973 and now abandoned.

The invention relates to new pharmacologically valuable derivatives of 1-phenoxy-3-amino-propane-2-ol of the general formula I

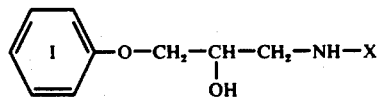

wherein X signifies

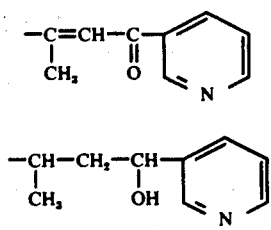

and the phenyl nucleus I may be mono-, di- or trisubstituted by alkyl, alkenyl, alkinyl, cycloalkyl, cycloalkenyl, alkoxy, alkenyloxy, alkinyloxy, phenyl, halogen, or the radical —$NR_1R_2$, in which $R_1$ stands for alkyl or acyl and $R_2$ for hydrogen or alkyl, together with their aldehyde condensation products and acid addition salts. The substituents of the phenyl nucleus I if more than one in number may be the same or different.

The invention also extends to processes for the production of the above compounds and to pharmaceutical preparations containing them.

Compounds of the invention in which X represents

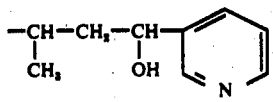

Within the scope of the present invention, the compounds of the general formula I are also understood to include possible stereoisomers and optically active compounds and mixtures thereof, particularly the racemate.

Preferred substituents for the phenyl nucleus I are alkyl with 1 to 4 carbon atoms, for example methyl, ethyl, propyl, tert. butyl;

Alkenyl with up to 6 carbon atoms, preferably vinyl, allyl, methyllyl, crotyl;

alkinyl with up to 6 carbon atoms, for example propargyl; cycloalkyl with a ring size of 5 to 8 carbon atoms, preferably cyclopentyl and cyclohexyl;

cycloalkenyl with a ring size of 5 to 8 carbon atoms, preferably cyclopentenyl;

alkoxy, alkenyloxy, and alkinyloxy containing in each case up to 5 carbon atoms, preferably methoxy, ethoxy, propoxy, butoxy, allyloxy, methallyloxy, propargyloxy, especially pentoxy;

halogen, particularly bromine or chlorine;

the radical —$NR_1R_2$, wherein $R_1$ stands for an alkyl radical having 1 or 2 carbon atoms, or an acyl containing up to 11 carbon atoms, and $R_2$ stands for hydrogen or alkyl having 1 or 2 carbon atoms. $R_1$ when an acyl radical is preferably an aryl or alkyl substituted carbonyl radical containing up to 11 carbon atoms which is derived from an aromatic or aliphatic carboxylic acid, for example formyl, acetyl, propionyl, butyryl, benzoyl, naphtoyl, phenylacetyl, or preferably acetyl or benzyl.

Within the scope of the present invention the compounds of the formula

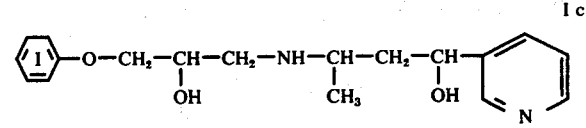

wherein the phenyl nucleus I is mono-substituted by methyl, phenyl, allyl, alkoxy with 1 to 5 carbon atoms, allyloxy, chloro, cyclopentyl, acetamino, or is di-substituted by chloro or methoxy, or is tri-substituted by methoxy, are particularly preferred.

The aldehyde condensation product of the compounds of the general formula I are oxazolidines of the formula I d

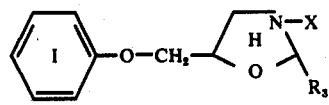

which are formed on the condensation of compounds of the general formula I with an aldehyde of the formula $$R_3\text{—CHO}$$

in which $R_3$ represents hydrogen or an alkyl radical containing up to 4 carbon atoms.

In the human or animal organism the aldehyde is split off from these condensation products, whereby the compounds of the general formula I, used for the preparation of these products are liberated.

The liberation of compounds of the general formula I from said condensation products is the reason that these condensation products may be used in the same way and for the same purpose as is the case with the compounds of the general formula I themselves on their acid addition salts.

Inorganic and organic acids are suitable for forming acid addition salts with the compounds of the general formula I. Suitable acids are, for example, hydrogen chloride, hydrogen bromide, phosphoric, sulphuric, oxalic, lactic, tartaric, acetic, salicylic, benzoic, citric, or adipic acid. Pharmaceutically acceptable acid addition salts are preferred.

Compounds of the general formula I may, for example, be prepared by the processes described below, while the phenyl nuclei I of the following structural formulae may in each case be substituted as indicated above in the general formula I.

Process A

A 1-phenoxy-3-amino-propane-2-ol of the general formula II is reacted with a compound of the general formula III to form a compound I according to the invention:

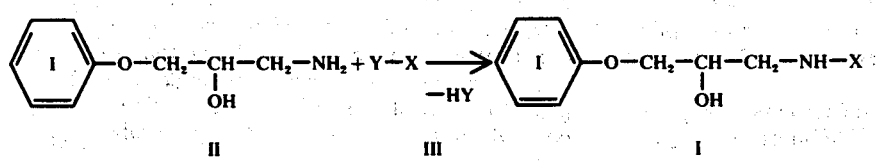

In this formula X has the meaning already indicated and Y indicates halogen, preferably chlorine or bromine, or, when X stands for

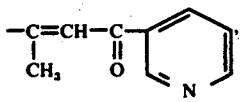

also for —OH, —OK, or —ONa.

Process B

A compound of the general formula IV is reacted with a compound of the general formula V to form a compound I according to the invention.

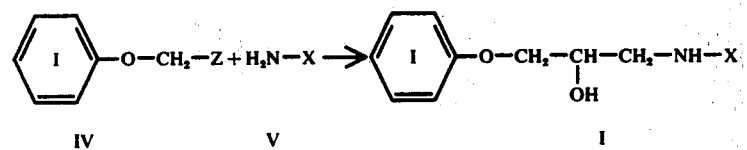

In this formula X has the meaning aleady indicated and Z denotes:

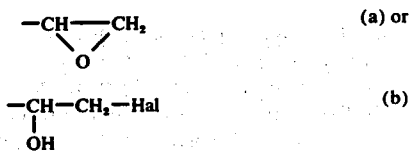

Hal stands for a halogen atom, preferably chlorine or bromine.

Process C

Compounds according to the invention of the general formula I can also be synthesized by reacting a compound of the general formula VI with a phenol of the general formula VII.

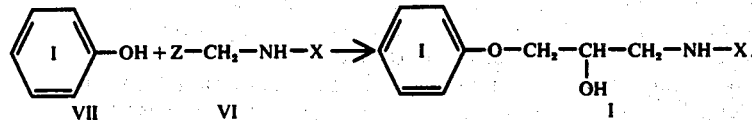

Z and X have the meanings already indicated.

Process D

The preferred compounds according to the invention in which X is

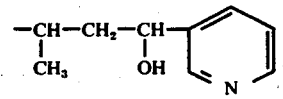

may in addition also be prepared by hydrogenating a compound of the general formula

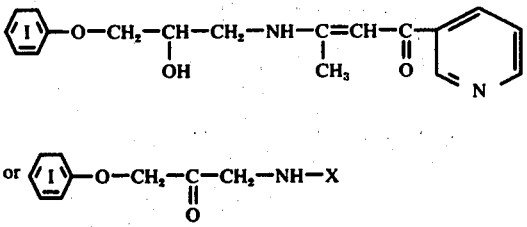

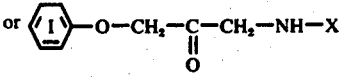

The various processes and the preparation of the starting products required to carry them out are explained more fully below.

The reaction according to process A is normally carried out in a suitable solvent or dispersion medium in which the reactants are dissolved or suspended. Such solvents or dispersion media are for example aromatic hydrocarbons such as benzene, toluene, xylene, ketones such as acetone or methyl ethyl ketone, halogenated hydrocarbons such as chloroform, carbon tetrachloride, chlorobenzene and methylene chloride, ethers such as tetrahydrofurane or dioxane, sulphoxides such as dimethylsulphoxide, tertiary acid amides such as dimethylformamide or N-methyl-pyrrolidone. Polar solvents such as alcohols are particularly useful, examples of suitable alcohols being methanol, ethanol, isopropanol and tertiary butanol. The reaction is carried out at a temperature between 20° and the reflux temperature of the solvent or dispersion medium used, often taking place at room temperature. If X stands for

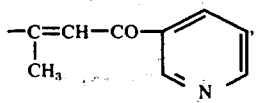

the reaction is accelerated by adding an acid, preferably hydrogen chloride, other suitable acids being for example formic acid, acetic acid, propionic acid or butyric acid, sulphonic acids such as benzenesulphonic acid and p-toluenesulphonic acid, or mineral acids such as sulphuric or phosphoric acid. When Y in Formula III signifies —OH, catalytic amounts of acid, for example acetic or formic acid, are sufficient. When Y represents —ONa or —OK, about 1 mole of the acid is added. The compound of the general formula II may instead also be used in the form of a salt, for example its hydrohalide. When Y stands for halogen, the compounds of the general formula III may also be used in the form of their hydrohalide. In process A the acid addition salts of compound I may be formed.

The pyridylbutenone compounds of the general formula IIIa

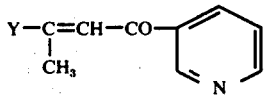

IIIa (in which X stands for

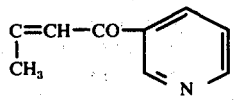

which are required as starting compounds can be obtained either by reacting a nicotinic acid ester, particularly nicotinic acid methyl or ethyl ester, with acetone under the conditions of an alkaline ester condensation, or reacting under similar conditions an acetic acid ester, particularly acetic acid methyl or ethyl ester, with 3-acetylpyridine. From the sodium or potassium salts of nicotinoylacetone which can be produced in this manner it is possible to form, by hydrolysis, the free nicotinoylacetone (Y = OH in formula IIIa) or the tautomeric form

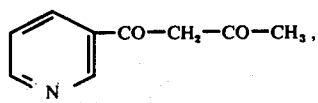

which in turn can be converted by means of suitable halogenation media, for example thionyl chloride, or phosphorus tribromide, into the corresponding 3-halogeno-1-(3-pyridyl)-but-2-en-1-one of the general formula IIIb (Hal = halogen, particularly Cl or Br).

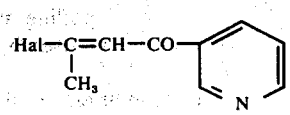

IIIb

Compounds of the general formula III, in which Y represents halogen (Hal), particularly bromine or chlorine, and X represents

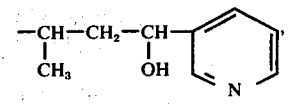

and which thus correspond to the general formula IIIc

IIIc

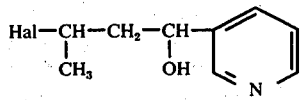

can be prepared from the corresponding compounds IIIb by hydrogenation, advantageously with complex hydrides, such as for example lithium aluminium hydride, sodium boron hydride, or the like.

The compounds of the general formula II required as starting compounds can be prepared by reacting a compound of the general formula IVa or IVb IVa

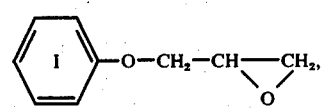

IVb

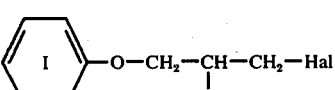

in which IVb Hal represents a halogen atom, particularly chlorine or bromine, or a mixture of a compound IVa and a compound IVb equally substituted in the phenyl nucleus I, with ammonia or substances splitting off ammonia. The reaction may be carried out under atmospheric pressure or elevated pressure at ambient temperature and may be accelerated or terminated by supplying heat, for example by heating to 70° C.

The compounds of the general formulae IVa and IVb can be prepared by reacting a phenol of the general formula VII

VII

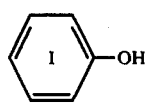

with an epihalogenhydrin, preferably with epichlorohydrin or epibromohydrin. Depending on the reaction conditions, this will result in the formation of a compound of the general formula IVa and IVb or a mixture of compounds of the general formulae IVa and IVb. For the purpose of further conversion the resulting reaction product may isolated with ammonia, or else may be further converted direct without isolation.

In the performance of process B it is also possible to use as the compound IV a mixture of the two compounds IVa and IVb which are similarly substituted in the phenyl nucleus I.

The reactions according to process B are carried out in a suitable solvent or dispersion agent at normal or elevated temperature. Examples of suitable solvents are the same as those listed for use in Process A. The reaction may be carried out at temperatures between 20° C and the reflux temperature of the solvent or dispersing agent used, and is often found to take place at between 40° and 50° C.

It may be advantageous to employ the starting compound of general formula V in up to 10-fold molar excess and/or to add the reactant of general formula IV in dissolved or suspended form to the dissolved or suspended starting compound of general formula V. The molar ratio of the compounds of general formulas IV and V may be 1:1 to 1:10 or even higher.

The reaction of compounds of the general formula IV*b* may be carried out in the presence of acid-binding media, such as potassium or sodium hydroxide, or without acid-binding media, the hydrohalides of compounds of the general formula I usually being obtained in the latter case.

In process C, instead of a single compound of the general formula VI it is possible to use a mixture, for example of compounds of the general formulae VI*a* and VI*b*

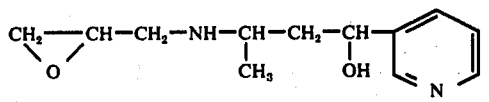
VI*a*

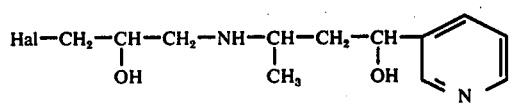
VI*b*

The reactions according to process C may be effected either in a solvent or dispersing agent as exemplified in connection with process A and in the presence of an acid binding agent such as potassium carbonate, sodium carbonate or sodium bicarbonate, or in an aqueous alkaline solution, for example in dilute sodium or potassium hydroxide solution. The reaction may be carried out at a temperature between 20° C and the reflux temperature of the solvent or dispersing agent used.

It may be advantageous to employ the starting compound of general formula VI in up to 10-fold molar excess and/or to add the reactant of general formula VII in dissolved or suspended form to the dissolved or suspended starting compound of general formula VI. The molar ratio of the compounds of general formula VII and VI may be 1:1 to 1:10 or even higher.

The compounds of the general formula VI can be prepared by reacting a compound of the general formula V with an epihalogenhydrin, preferably with epichlorohydrin or epibromohydrin. Depending on the reaction conditions, this will result in the formation of a compound of the general formula VI*c* and VI*d*

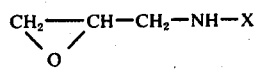
VI*c*

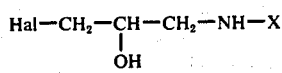
VI*d*

The resulting reaction product may be isolated or else may be further converted direct without isolation.

From the compounds I*a* according to the invention

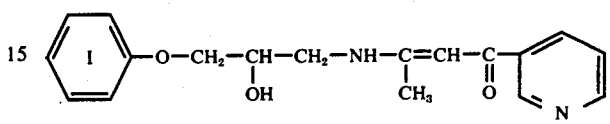

it is possible by hydrogenation to prepare compounds I*b* according to the invention

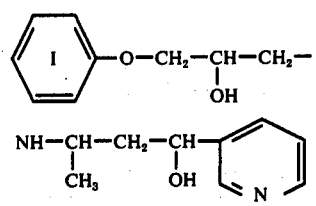

For the purpose of hydrogenation it is advantageous to use complex hydrides, such as for example lithium aluminium hydride, sodium boron hydride and the like. The reaction is performed under the known reaction conditions for the use of these hydrides, normally in a mixture of alcohol and water at ordinary or elevated temperature, for example by boiling under reflux. The hydrogenation may also be effected catalytically, for example using a palladium-carbon catalyst.

Compounds of the general formula VIII may be similarly hydrogenated. Starting compounds of the general formula VIII can be obtained by reacting a compound of the general formula IX with a compound of the general formula III*d*:

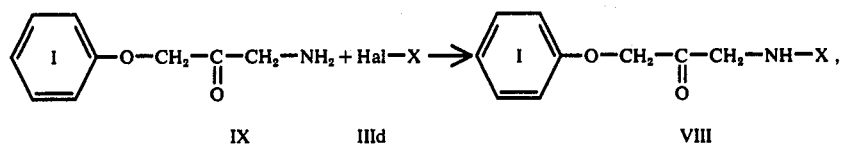

IX      III*d*      VIII

Hal in the general formula III*d* denoting halogen, preferably chlorine. The general formula III*d* comprises the compounds of the general formulae III*b* and III*c*.

The reactions between the compounds of the general formulae IX and III*d* (or III*c* or III*b*) are effected in solvents such as benzene, toluene, chloroform, methylene chloride or dioxane, at normal or elevated temperature in the presence of at least molar amounts of acid-binding media, such as sodium or potassium hydroxide or without the presence of acid-binding media, the hydrohalides of the compounds VIII usually being obtained in the latter case.

For the preparation of compounds of the general formula IX, for example, a phenol of the general formula VII is reacted with a halogenoacetone of the general formula X, in which Hal denotes a halogen atom, preferably bromine or chlorine, and the resulting product of the general formula XI is brominated or chlorinated, thereby obtaining a compound of the general formula XII in which Hal denotes bromine or chlorine, this compound being converted into a compound of the general formula IX using ammonia or a compound yielding ammonia:

rauwolfia alkaloids; bronchodilators, and sympathomimetic media, such as for example isopremaline and ephedrine.

To demonstrate the pharmalogical effect of compounds of the invention, the left ventricular blood pressure and its time differential (dp/dt), was continuously measured and registered on narcotised dogs by means of a catheter tip manometer.

Isoproterenol ($0.5 \cdot 10^{-6}$ gram/kg i.v.) was injected at

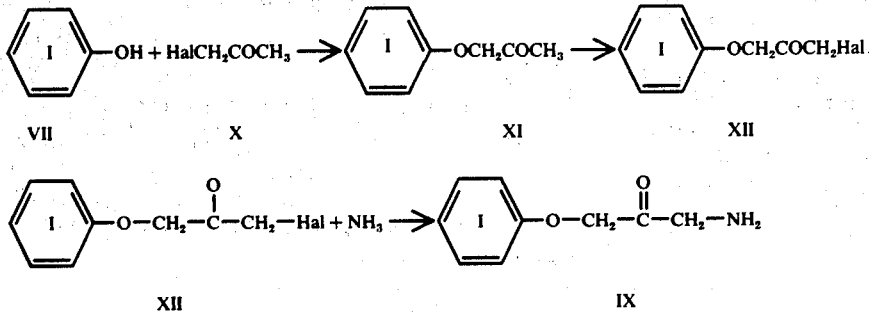

Aldehyde condensation products of formula Ic are obtained by reacting compounds of the general formula I with an aldehyde of the formula $R_3$—CHO, in which $R_3$ denotes hydrogen or a low alkyl radical, in a diluent or solvent, for example ethanol, preferably in the presence of an acid catalyst, for example acetic acid or hydrochloric acid, and preferably at elevated temperature. The water formed by the reaction can be removed with the aid of entraining agent, for example benzene, by azeotropic distillation, or with the aid of a dehydration medium, such as anhydrous potassium carbonate.

The acid addition salts of the compounds of the general formula I can be prepared from the components known per se. In this case it is generally advantageous to use a diluent, while with an excess of acid the di-salts of the compounds of the general formula I are generally obtained. The monoacid addition salts are obtained either by controlled addition of only 1 mole of acid or by partial hydrolysis of the di-acid addition salts.

The compounds of the general formula I according to the invention, their aldehyde condensation products Ic, and their pharmaceutically acceptable acid addition salts have valuable pharmaceutical properties. Thus, for example, they are suitable for the treatment or prophylaxis of diseases of the heart. The preferred compounds possess very pronounced β-adrenalytic or anti-arythmic properties. The compounds according to the invention can therefore be used as pharmaceutical preparations, by themselves, mixed with one another, or mixed with pharmaceutically acceptable diluents or carriers. The pharmaceutical preparations may be in the form of, for example, tablets, capsules, aqueous or oily solutions or suspensions, emulsions, injectable aqueous or oil solutions or suspensions, dispersible powders, or aerosol mixtures. In addition to the compounds of the general formula I according to the invention, the pharmaceutical preparations may also contain one or more other pharmaceutically active substances, for examples sedatives, such as for example luminal, meprobamate, and chloropromazine; vasodilators, such as for example glycerine trinitrate and carbochromen; diuretics, such as for example chlorothiazide; cardiotonics, such as for example digitalis preparations; hypotension media, such as for example intervals of 15 minutes before and after increasing doses of the test substance. The changes of the dp/dt max. after isoproterenol were determined before and after the intravenous administration of the test substance. These values were used to calculate the $ED_{50}$. The doses quoted in each case are the cumulative doses of the test substance. The values obtained are shown in the table which follows:

| Substance | $ED_{50}$ dp/dt mg/kg i.v. |
|---|---|
| 1-(3'-β-pyridyl-3'-hydroxy-1'-methyl-propylamino)-3-(o-ethoxyphenoxy)-propan-2-ol | 0.0151 |
| 1-(3'-β-pyridyl-3'-hydroxy-1'-methyl-propylamino)-3-(o-allyloxyphenoxy)-propan-2-ol | 0.0080 |
| 1-(3'-β-pyridyl-3'-hydroxy-1'-methyl-propylamino)-3-(o-chlorophenoxy)-propan-2-ol | 0.0082 |
| 1-(3'-β-pyridyl-3'-hydroxy-1'-methyl-propylamino)-3-(m-methoxyphenoxy)-propan-2-ol | 0.0120 |
| 1-(3'-β-pyridyl-3'-hydroxy-1'-methyl-propylamino)-3-(p-ethoxyphenoxy)-propan-2-ol | 0.0448 |
| 1-(3'-β-pyridyl-3'-hydroxy-1'-methyl-propylamino)-3-(m-methylphenoxy)-propan-2-ol | 0.0175 |
| 1-(3'-β-pyridyl-3'-hydroxy-1'-methyl-propylamino)-3-(o-allylphenoxy)-propan-2-ol | 0.0178 |
| 1-(3'-β-pyridyl-3'-hydroxy-1'-methyl-propylamino)-3-(o-methoxyphenoxy)-propan-2-ol | 0.0060 |
| 1-(3'-β-pyridyl-3'-hydroxy-1'-methyl-propylamino)-3-(p-propoxyphenoxy)-propan-2-ol | 0.0167 |
| 1-(3'-β-pyridyl-3'-hydroxy-1'-methyl-propylamino)-3-(p-acetamino-phenoxy)-propan-2-ol | 0.0146 |
| 1-(3'-β-pyridyl-3'-hydroxy-1'-methyl-propylamino)-3-(p-chlorophenoxy)-propan-2-ol | 0.0300 |
| 1-(3'-β-pyridyl-3'-hydroxy-1'-methyl-propylamino)-3-(p-pentoxyphenoxy)-propan-2-ol | 0.0184 |
| (-)-1-(3'-β-pyridyl-3'-hydroxy-1'-methyl-propylamino)-3-(o-ethoxyphenoxy)-propan-2-ol, laevo-rotatory | 0.0026 |
| Comparison preparation: Propranolol | 0.0561 |

Substances having a strongly negative-inotropic intrinsic action such as PROPRANOLOL are assessed adversely in clinical practice, since they are capable of causing an acute cardiac insufficiency or liable to intensify an already existing cardiac insufficiency. The table which follows shows that compounds according to the invention have a less strong inotropic intrinsic action or are even inert (that is to say neither positively nor negatively inotropic) or positively inotropic:

| Substance | Intrinsic action on the dp/dt |
|---|---|
| 1-(3'-β-Pyridyl-3'-hydroxy-1'-methyl-propyl-amino)-3-(o-ethoxyphenoxy)-propan-2-ol | 0 |
| 1-(3'-β-Pyridyl-3'-hydroxy-1'-methyl-propyl-amino)-3-(o-allyloxyphenoxy)-propan-2-ol | − |
| 1-(3'-β-Pyridyl-3'-hydroxy-1'-methyl-propyl-amino)-3-(o-cyclopentylphenoxy)-propan-2-ol | − |
| 1-(3'-β-Pyridyl-3'-hydroxy-1'-methyl-propyl-amino)-3-(p-methoxyphenoxy)-propan-2-ol | ++ |
| 1-(3'-β-Pyridyl-3'-hydroxy-1'-methyl-propyl-amino)-3-(p-butoxyphenoxy)-propan-2-ol | — |
| 1-(3'-β-Pyridyl-3'-hydroxy-1'-methyl-propyl-amino)-3-(o-chlorophenoxy)-propan-2-ol | 0 |
| 1-(3'-β-Pyridyl-3'-hydroxy-1'-methyl-propyl-amino)-3-(m-methoxyphenoxy)-propan-2-ol | — |
| 1-(3'-β-Pyridyl-3'-hydroxy-1'-methyl-propyl-amino)-3-(p-ethoxyphenoxy)-propan-2-ol | — |
| 1-(3'-β-Pyridyl-3'-hydroxy-1'-methyl-propyl-amino)-3-(m-methylphenoxy)-propan-2-ol | — |
| 1-(3'-β-Pyridyl-3'-hydroxy-1'-methyl-propyl-amino)-3-(o-phenylphenoxy)-propan-2-ol | 0 |
| 1-(3'-β-Pyridyl-3'-hydroxy-1'-methyl-propyl-amino)-3-(o-allylphenoxy)-propan-2-ol | — |
| 1-(3'-β-Pyridyl-3'-hydroxy-1'-methyl-propyl-amino)-3-(3',4',5'-trimethoxyphenoxy)propan-2-ol | — |
| 1-(3'-β-Pyridyl-3'-hydroxy-1'-methyl-propyl-amino)-3-(2',3'-dimethoxyphenoxy)-propan-2-ol | − |
| 1-(3'-β-pyridyl-3'-hydroxy-1'-methyl-propyl-amino)-3-(2',6'-dichlorophenoxy)-propan-2-ol | ++ |
| 1-(3'-β-pyridyl-3'-hydroxy-1'-methyl-propyl-amino)-3-(o-methoxyphenoxy)-propan-2-ol | +++ |
| 1-(3'-β-pyridyl-3'-hydroxy-1'-methyl-propyl-amino)-3-(p-propoxyphenoxy)-propan-2-ol | ++ |
| 1-(3'-β-pyridyl-3'-hydroxy-1'-methyl-propyl-amino)-3-(p-acetaminophenoxy)-propan-2-ol | — |
| 1-(3'-β-pyridyl-3'-hydroxy-1'-methyl-propyl-amino)-3-(p-chlorophenoxy)-propan-2-ol | − |
| 1-(3'-β-pyridyl-3'-hydroxy-1'-methyl-propyl-amino)-3-(p-pentoxyphenoxy)-propan-2-ol | 0 |
| (-)-1-(3'-β-pyridyl-3'-hydroxy-1'-methyl-propylamino)-3-(p-ethoxyphenoxy)-propan-2-ol, laevo-rotatory | 0 |
| Control preparation Propranolol | —— |

In the table the symbols denote the following:
+ = positively inotropic
− = negatively inotropic
0 = inert The number of − and + signs indicates the strength of the effect.

The manufacture of the compounds of the general formula I is explained in more detail in relation to the examples which follow. The compounds are frequently oils which cannot be distilled, so that in some cases a melting point cannot be quoted. However, in all cases the indicated structure has been confirmed by molecular analysis and/or by infra-red or nuclear response spectroscopy.

EXAMPLE 1

5.1 g of 1-amino-3-(o-allyloxyphenoxy)-propan-2-ol hydrochloride

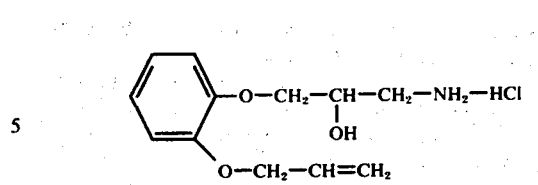

are suspended in 50 ml of ethanol, 4 g of the potassium salt of 2-nicotinoyl-1-methyl-vinyl alcohol

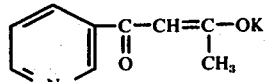

are then added and the mixture is stirred for 24 hours at room temperature. The suspension is filtered off and the residue is washed with ethanol. The filtrate, together with the wash alcohol is concentrated in vacuo. An oil is left, which solidifies after a short time. The oil which has solidified, together with the residue left on washing with alcohol, is repeatedly triturated with water and then recrystallised from ethanol. 1-(2-Nicotinoyl-1-methyl-vinylamino)-3-(o-allyloxyphenoxy)-propan-2-ol of the formula

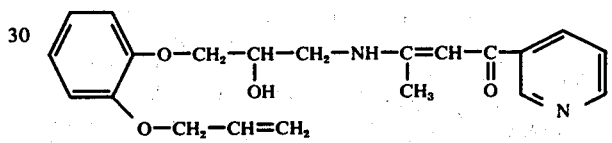

is thus obtained.
Melting point. 107° C
Analysis: ($C_{21}H_{24}N_2O_4$). Calculated: C, 68.5; H, 6.5; N, 7.6. Found: C, 67.9; H, 6.3; N, 7.7.
Yield: 4.1 g = 56% of theory.

The requisite potassium salt of nicotinoylacetone can be manufactured as follows:

22.4 g of potassium tert.-butylate are suspended in 150 ml of anhydrous benzene, a mixture of 18.3 g of ethyl acetate and 24.2 g of 3-acetylpyridine is then slowly added dropwise at 10° C, whilst stirring, and the mixture is subsequently left for 24 hours at room temperature. The product is then filtered off, washed twice with anhydrous benzene, then twice with anhydrous ethanol and finally twice with diethyl ether. The potassium salt of nicotinoylacetone is thus obtained in a yield of 77% of theory.

The sodium salt of nicotinoylacetone can also be manufactured from nicotinic acid ethyl ester and anhydrous acetone in the presence of sodium ethylate, in a known manner, for example according to A Ferenczy, Monatshefte fur Chemie, page 674 (1897).

The requisite 1-amino-3-(o-allyloxyphenoxy)-propan-2-ol can be manufactured as follows:

60 g of 1-(o-allyloxyphenoxy)-2,3-epoxy-propane

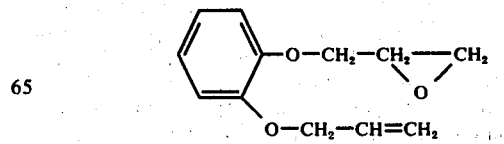

(manufactured from o-allyloxyphenol and epichlorohydrin in the presence of potassium carbonate, in acetone) are dissolved in 600 ml of methanol, 300 ml of liquid ammonia are added and the mixture is stirred for 3 hours in an autoclave at 70° C. Thereafter it is concentrated, the residue is dissolved in benzene, the solution is twice extracted with dilute hydrochloric acid, the aqueous acid phase is separated off, rendered alkaline and extracted three times with benzene, and the combined benzene phases are concentrated. The solid residue is recrystallised once from benzene. 1-Amino-3-(o-allyloxyphenoxy)-propan-2-ol

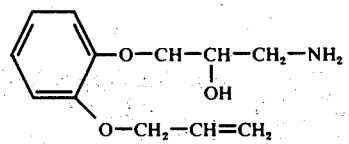

is thus obtained in a yield of 67% of theory.

Melting point: 89° C.

The base can be converted into 1-amino-3-(o-allyloxyphenoxy)-propan-2-ol hydrochloride, of melting point 110° C, by means of hydrochloric acid in ether, in the usual manner.

EXAMPLE 2

4.8 g of 1-amino-3-(p-butoxyphenoxy)-propan-2-ol

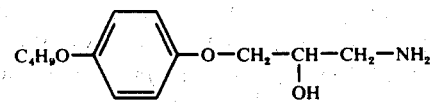

are dissolved in 60 ml of anhydrous benzene and 5.7 g of anhydrous potassium carbonate are added. A mixture of 4.4 g of 2-nicotinoyl-1-methyl-vinyl chloride hydrochloride of the formula

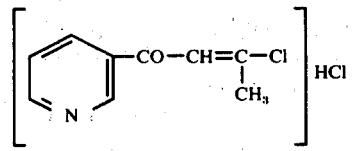

(manufactured from the sodium salt of nicotinoylacetone, which is first converted, with HCl gas, into the hydrochloride of free nicotinoylacetone and then, with thionyl chloride, into the nicotinoyl-methyl-vinyl chloride hydrochloride) in 50 ml of anhydrous benzene is added to the first mixture, whilst cooling and stirring, and the whole is subsequently stirred for a further 24 hours at room temperature. The mixture is then filtered, the residue is dissolved in water, and the solution is rendered alkaline with sodium carbonate and is repeatedly extracted with chloroform. The chloroform extracts, together with the original benzene filtrate, are concentrated in vacuo at approx. 10 to 14 mm Hg. After repeated recrystallisation from aqueous ethanol, 1-(2-nicotinoyl-1-methyl-vinylamino)-3-(p-butoxyphenoxy)-propan-2-ol is thus obtained.

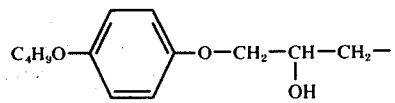

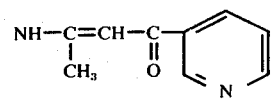

Melting point: 124° C

Analysis: ($C_{22}H_{28}N_2O_4$). Calculated: C, 68.8; H, 7.3; N, 7.3. Found: C, 68.6; H, 7.1; N, 7.2.

Yield: 5.6 g = 73% of theory.

1-Amino-3-(p-butoxyphenoxy)-propan-2-ol, used as the starting product, can be obtained by heating p-butoxyphenol with epichlorohydrin and potassium carbonate in anhydrous acetone and further reaction of the 1-(p-butoxyphenoxy)-2,3-epoxy-propane thus obtained (boiling point 130° to 135° C at 0.4 mm; melting point: 34° C) with ammonia in an autoclave at 70° C. (Melting point: 107° C).

1-(2-Nicotinoyl-1-methyl-vinylamino)-3-(p-butoxyphenoxy)-propan-2-ol is also obtained if 1-amino-3-(p-butoxypheoxy)-propan-2-ol, instead of being reacted with 2-nicotinoyl-1-methyl-vinyl chloride hydrochloride and potassium carbonate, is reacted with a molar amount of nicotinoylacetone (manufactured according to L. F. Kuick and H. Adkins, J. Am. Chem. Soc. 57, 143 (1935)) and a catalytic amount of formic acid in ethanol solution, whilst boiling under reflux (yield: 68% of theory).

EXAMPLE 3

4.2 g of (-)-1-amino-3-(o-ethoxyphenoxy)-propan-2-ol (laevo-rotatory)

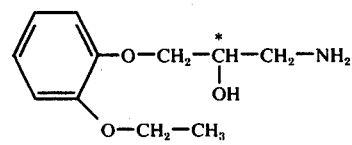

are dissolved in 30 ml of ethanol, 3.3 g of the nicotinoyl-acetone

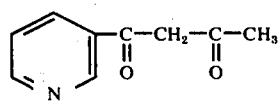

are then added and the mixture is heated for 4 hours under reflux, with addition of 1 drop of formic acid as the catalyst. The clear solution is cooled to room temperature and concentrated in a water pump vacuum. An oil is left, which solidifies after a short time. The solid product is recrystallised from toluene. (-)-1-(2-Nicotinoyl-1-methyl-vinylamino)-3-(o-ethoxyphenoxy)-propan-2-ol (laevo-rotatory) is thus obtained

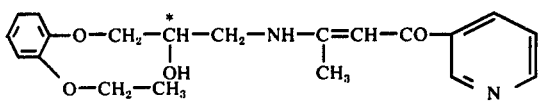

Melting point: 94° C

Analysis. ($C_{20}H_{24}N_2O_4$). Calculated: C, 67.4; H, 6.7; N, 7.9. Found: C, 67.1; H, 6.7; N, 7.8.

Yield: 5.9 g = 83% of theory

Optical rotation = −70°

The requisite (−)-1-amino-3-(o-ethoxyphenoxy)-propan-2-ol (laevo-rotatory) can be manufactured as follows:

20 g of 1-amino-3-(o-ethoxyphenoxy)-propan-2-ol (racemate) are dissolved in 295 ml of isopropanol and a solution of 7.1 g of L(+)-tartaric acid in 100 ml of isopropanol is added, whereupon a voluminous white precipitate separates out. The white product is filtered off, well washed with isopropanol and dried in vacuo. 26.7 g of the tartrate (95% of theory) of 1-amino-3-(o-ethoxyphenoxy)-propan-2-ol are thus obtained, having an optical rotation = +12°.

These 26.7 g are recrystallised 3 times from a mixture of 40 parts of dimethylformamide and 10 parts of water. This finally yields the laevo-rotatory tartrate of 1-amino-3-(o-ethoxyphenoxy)-propan-2-ol (2 mols of amine per 1 mol of tartaric acid) of optical rotation −1° (melting point: 201° C).

4 g of the finely powdered salt are suspended in 60 ml of dioxane and $NH_3$ gas is passed in for ½ hour at room temperature (the heat of the reaction is removed by cooling). The ammonium tartrate is filtered off and the dioxane filtrate is concentrated in vacuo. The solid white residue is recrystallised from ligroin. Laevo-rotatory (−)-1-amino-3-((o-ethoxyphenoxy)-propan-2ol of melting point 87° C is thus obtained.

Yield = 2.6 g = 88% of theory (calculated for the laevo-rotatory tartrate), optical rotation = −5°.

EXAMPLE 4

3.6 g of 1-(4'-methoxy-phenoxy)-2,3-epoxypropane

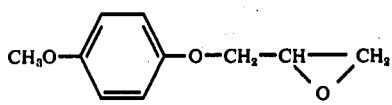

(prepared by heating 4-methoxyphenol with epichlorohydrin and potassiium carbonate in anhydrous benzene; boiling point at 1.25 mm: 140° to 145° C) and 17 g of 1-(β-pyridyl)-3-aminobutan-1-ol

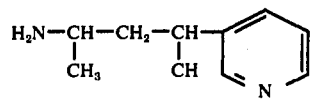

in 65 ml of ethanol are heated for 5 hours under reflux. The mixture is then concentrated in vacuo (approx. 10 to 14 mm Hg), the residue is dissolved in dilute hydrochloric acid, the solution is repeatedly washed with benzene and rendered alkaline with sodium carbonate and the alkaline solution is extracted with chloroform. The chloroform extracts are washed with water, dried with sodium sulphate and concentrated in vacuo (approx. 10 to 14 mm Hg).

1-(3'-β-Pyridyl-3'-hydroxy-1'-methyl-propylamino)-3-(p-methoxyphenoxy)-propan-2-ol is thus obtained as a viscous yellow oil.

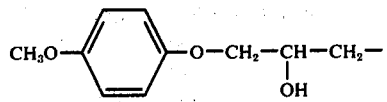

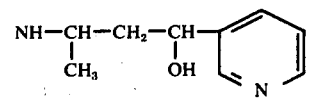

Analysis: ($C_{19}H_{26}N_2O_4$). Calculated: C, 65.9; H, 7.5 N, 8.1. Found: C, 65.5 H, 7.5; N, 7.9.

Yield: 3.3 g = 48% of theory 1-(β-Pyridyl)-3-amino-butan-1-ol, required as the starting product, can be manufactured as follows:

The potassium salt of nicotinoylacetone is first synthesised, as indicated in Example 1.

2 g of the potassium salt is nicotinoylacetone are then suspended in 50 ml of ethanol and 1.6 g of benzylamine hydrochloride are added and the mixture is stirred for 24 hours at room temperature. The suspension is filtered and the residue is washed with ethanol. The filtrate together with the wash alcohol are concentrated in vacuo. An oil is left, which solidifies after a short time. The solidified oil, together with the residue left on washing with alcohol, is repeatedly triturated with water and then recrystallised from ethanol. N-(2-Nicotinoyl-1-methyl-vinylamino)-benzylamine is thus obtained.

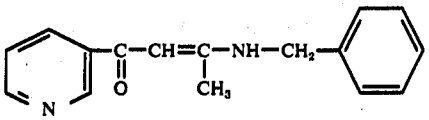

On reduction with sodium borohydride, this compound gives a 62% yield of 1-(β-pyridyl)-3-benzylamino-butan-1-ol (oil)

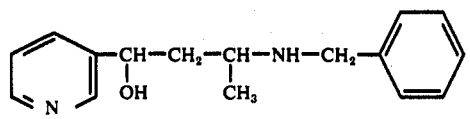

which can be debenzylated in the usual manner with hydrogen in an autoclave to give 1-(β-pyridyl)-3-amino-butan-1-ol (viscous oil)

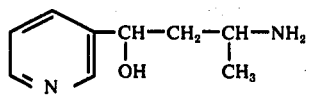

1-(β-Pyridyl)-3-amino-butan-1-ol can also be prepared as follows:

5 g of 2-nicotinoyl-1-methyl-vinylamine

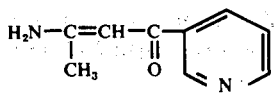

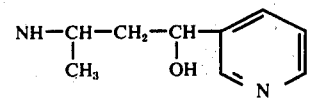

are dissolved in 50 ml of ethanol and a total of 6 g of sodium borohydride is added in portions over the course of 6 hours at 70° C, whilst stirring. The mixture is then kept at 70° C for a further 10 hours. It is then concentrated, the residue is taken up in chloroform/water, and the chloroform phase is separated off, dried and concentrated in vacuo (10 to 14 mm Hg). The oil which remains is distilled. The fraction which passes over between 125° and 150° C at 0.3 mm Hg is subsequently dissolved in dioxane and the solution is mixed with a solution of tartaric acid in dioxane. The slight hygroscopic tartrate which precipitates is filtered off, recrystallised from dimethylformamide/ethyl acetate and subsequently converted into the free base. 1-(β-Pyridyl)-3-amino-butan-1ol is thus obtained in 73% yield.

The 2-nicotinoyl-1-methyl-vinylamine required for the reduction can be manufactured as follows:

7.5 g of nicotinoylacetone are dissolved in 45 ml of anhydrous ethanol and after addition of 20 ml of ammonia the mixture is stirred in an autoclave for 3 days at 50° C. On concentrating the clear solution, an oil is left, which solidifies after a short time. After recrystallisation from toluene, 2-nicotinoyl-1-methyl-vinylamine (melting point 82° C) is thus obtained in 91% yield.

EXAMPLE 5

2.5 g of p-methoxyphenol, 2.8 g of potassium hydroxide and 80 ml of anhydrous acetone are heated under reflux. A solution of 4.5 g of 1-(3-β-pyridyl-3-hydroxy-1-methyl-propylamino)-2,3-epoxypropane

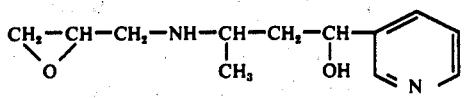

in 100 ml of anhydrous acetone is added dropwise to this mixture. The whole is then heated for a further 4 hours under reflux and is thereafter cooled and filtered, and the filtrate is concentrated in vacuo (approx. 10 to 14 mm Hg). An oily residue is left, which is dissolved in dilute hydrochloric acid. The solution is repeatedly washed with benzene and rendered alkaline with sodium carbonate and the alkaline solution is extracted with chloroform. The chloroform extrcts are washed with water, dried with sodium sulphate and concentrated in vacuo (approx. 10 to 14 mm Hg). 1-(3'-β-Pyridyl-3'-hydroxy-1'methyl-propylamino)-3-(p-methoxyphenoxy)-propan-2-ol is thus obtained as a viscous yellow oil.

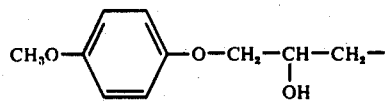

Analysis: (C₁₉H₂₆N₂O₄). Calculated: C, 65.9; H, 7.5; N, 8.1. Found: C, 65.5; H, 7.5; N, 7.9.

1-(3-β-Pyridyl-3-hydroxy-1-methyl-propylamino)-2,3-epoxypropane required as the starting product, can be obtained from 1-(β-pyridyl)-3-amino-butan-1-ol by reaction with epichlorohydrin in methanolic solution at 40° C.

EXAMPLE 6

3.6 g of 1-(2-nicotinoyl-1-methyl-vinylamino)-3-(o-ethoxyphenoxy)-propan-2-ol

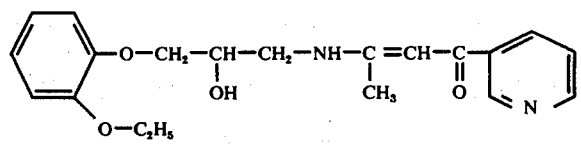

are dissolved in 40 ml of methanol and 10 ml of water, 2.0 g of sodium borohydride are added and the mixture is stirred for 3 hours at room temperature. Thereafter it is stirred for 13 hours at 70° C, with a further 3.5 g of sodium borohydride being added in portions, the mixture is then concentrated in vacuo (approx. 10 to 14 mm Hg), the residue is taken up in 60 ml of water and 60 ml of chloroform, the chloroform phase is separated off, the aqueous solution is extracted twice more with chloroform, and the chloroform solution is washed with water, dried with sodium sulphate and concentrated in vacuo (approx. 10 to 14 mm Hg). The oil which remains is dissolved in dilute hydrochloric acid, the solution is extracted three times with benzene and the acid aqueous phase is then rendered alkaline with sodium carbonate and finally extracted three times with chloroform. The chloroform solution is washed with water, dried and concentrated in vacuo (approx. 10 to 14 mm Hg).

1-(3'-β-Pyridyl-3'-hydroxy-1'-methyl-propylamino)-3-(o-ethoxyphenoxy)-propan-2-ol is thus obtained as a thick yellow oil.

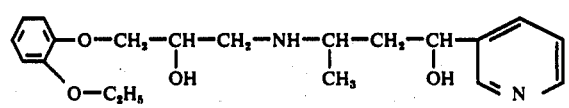

Analysis: (C₂₀H₂₈N₂O₄). Calculated: C, 66.7; H, 7.8; N, 7.8. Found: C, 66.8; H, 7.9; N, 7.5.

Yield: 4.9 g = 68% of theory

The requisite starting product can be manufactured as follows:

2.1 g of 1-amino-3-(o-ethoxyphenoxy)-propan-2-ol

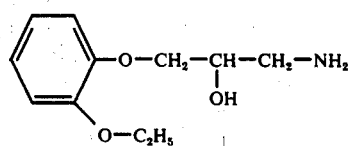

together with 1.7 g of nicotinoylacetone

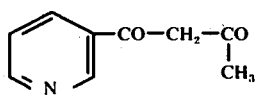

are dissolved in 30 ml of ethanol and the solution is heated for 3 hours under reflux, with addition of 1 drop of formic acid. It is then concentrated in vacuo (approx. 10 to 14 mm Hg). An oil is left, which after a short time solidifies. After one recrystallisation from toluene, N-[2-nicotinoyl-1-methyl-vinyl]-3-(o-ethoxyphenoxy)-2-hydroxy-propylamine of melting point: 111° C is thus obtained in 91% yield.

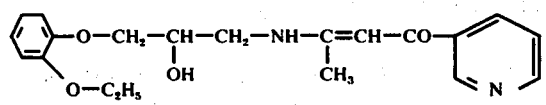

$(C_{20}H_{24}N_2O_4)$ Calculated: C, 67.4; H, 6.7; N, 7.9. Found: C, 67.1; H, 6.5; N, 8.0.

The nicotinoylacetone required as the starting product can be manufactured by condensation of nicotinic acid ethyl ester and absolute acetone under basic conditions in a known manner, for example according to A. Ferenczy, Monatshefte fur Chemie, page 674 (1897).

The 1-amino-3-(o-ethoxyphenoxy)-propan-2-ol required as the starting product can be manufactured as follows:

20 g of 1-(o-ethoxyphenoxy)-2,3-epoxy-propane

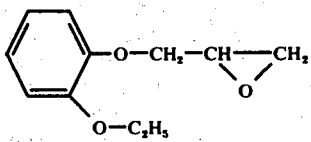

(manufactured from o-ethoxyphenol and epichlorohydrin in the presence of potassium carbonate and acetone, boiling point: 135° to 140° C at 3 to 4 mm Hg) are dissolved in 200 ml of methanol, 150 ml of liquid ammonia are added and the mixture is stirred for 5 hours in an autoclave at 70° C. Thereafter it is concentrated, the residue is dissolved in toluene, the solution is twice extracted with dilute hydrochloric acid, the aqueous acid phase is separated off, rendered alkaline and extracted three times with toluene, and the combined toluene phases are concentrated. The solid residue is recrystallised from benzene.

1-Amino-3-(o-ethoxyphenoxy)-propan-2-ol is obtained in a yield of 86% of theory. Melting point: 90° C.

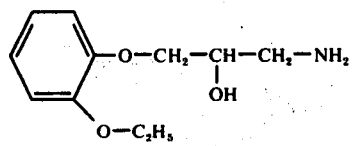

EXAMPLE 7

Analogously to the instructions in Example 6, reduction of 1-(2-nicotinoyl-1-methyl-vinylamino)-3-(p-butoxyphenoxy)-propan-2-ol with sodium borohydride yields 1-(3'-β-pyridyl-3'-hydroxy-1'-methyl-propylamino)-3-(p-butoxyphenoxy)-propan-2-ol (a viscous oil) of the formula

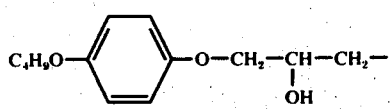

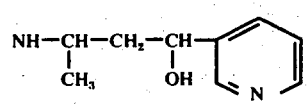

Analysis: $(C_{22}H_{32}N_2O_4)$. Calculated: C, 68.0; H, 8.3; N, 7.2. Found: C, 68.2; H, 8.1; N, 7.3.

The starting product required can be manufactured according to Example 2.

EXAMPLE 8

7 g of (-)-1-2-nicotinoyl-1-methyl-vinylamino-3-(o-ethoxyphenoxy)-propan-2-ol (laevo-rotatory, −70°)

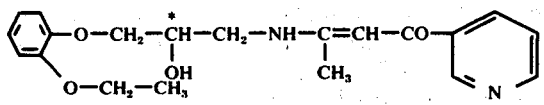

are dissolved in 70 ml of ethanol, the solution is heated to 80° C and at this temperature 3.8 g of sodium borohydride are added in small portions over the course of 2 hours and the mixture is subsequently heated for a further 8 hours at 80° C.

The mixture is concentrated in a water pump vacuum. The residue is taken up in 50 ml of water and 50 ml of chloroform, the chloroform phase is separated off, the aqueous solution is extracted twice more with chloroform and the chloroform solution is dried with sodium sulphate and concentrated in a water pump vacuum.

A small amount of impurity is distilled from the oil which remains, in vacuo at 0.1 mm Hg, the impurity passing over at a temperature of up to 134° C. The oily distillation residue is dissolved in anhydrous toluene, a pinch of animal charcoal is added, the mixture is filtered through a double filter, the filtrate is concentrated in a water pump vacuum and the residual oil is dried in vacuo at 60° C. (−)-1-β-Pyridyl-3-[3-(o-ethoxyphenoxy)-2-hydroxy-propylamino]-butan-1-ol (laevo-rotatory) is thus obtained as a thick yellow oil, in 78% yield.

Optical rotation = −7°

Calculated: C, 66.7; H, 7.8; N, 7.8; O, 17.8. Found: C, 66.7; H, 8.0; N, 7.9; O, 17.7.

The compounds listed in the table which follows were manufactured analogously to Examples 1 to 8.

| (R₄)ₓ | X | |
|---|---|---|
| 2-O—CH₂—CH=CH₂ | —CH—CH₂—CH—3—Py<br>  \|            \|<br>  CH₃      OH | Oil |
| 2-OC₂H₅ | —C=CH—CO—3—Py<br>  \|<br>  CH₃ | M.p.: 111° C |
| 2-cyclopentyl | —C=CH—CO—3—Py<br>  \|<br>  CH₃ | M.p.: 116° C |
| 2-cyclopentyl | —CH—CH₂—CH—3—Py<br>  \|            \|<br>  CH₃      OH | Viscous oil |
| 4-OCH₃ | —C=CH—CO—3—Py<br>  \|<br>  CH₃ | M.p.: 117° C |
| 3-CH₃ | —C=CH—CO—3—Py<br>  \|<br>  CH₃ | M.p.: 85° C |
| 3-CH₃ | —CH—CH₂—CH—3—Py<br>  \|            \|<br>  CH₃      OH | Oil |
| 4-CH₃—CO—NH | —C=CH—CO—3—Py<br>  \|<br>  CH₃ | M.p.: 166° C |
| 4-CH₃—CO—NH | —CH—CH₂—CH—3—Py<br>  \|            \|<br>  CH₃      OH | Oil |
| 2-Cl | —C=CH—CO—3—Py<br>  \|<br>  CH₃ | M.p.: 177° C |
| 2-Cl | —CH—CH₂—CH—3—Py<br>  \|            \|<br>  CH₃      OH | Oil |
| 2-C₆H₅ | —C=CH—CO—3—Py<br>  \|<br>  CH₃ | M.p.: 123° C |
| 2-C₆H₅ | —CH—CH₂—CH—3—Py<br>  \|            \|<br>  CH₃      OH | Oil |
| 3,4,5-(OCH₃)₃ | —C=CH—CO—3—Py<br>  \|<br>  CH₃ | M.p.: 118° C |
| 3,4,5-(OCH₃)₃ | —CH—CH₂—CH—3—Py<br>  \|            \|<br>  CH₃      OH | Oil |
| 3-OCH₃ | —C=CH—CO—3—Py<br>  \|<br>  CH₃ | M.p.: 96° C |
| 3-OCH₃ | —CH—CH₂—CH—3—Py<br>  \|            \|<br>  CH₃      OH | Oil |
| 2-OCH₃, 4-CH₂—CH=CH₂ | —C=CH—CO—3—Py<br>  \|<br>  CH₃ | M.p.: 153° C |
| 2-OCH₃, 4-CH₂—CH=CH₂ | —CH—CH₂—CH—3—Py<br>  \|            \|<br>  CH₃      OH | Oil |
| 4-C₂H₅ | —C=CH—CO—3—Py<br>  \|<br>  CH₃ | M.p.: 114° C |
| 4-C₂H₅ | —CH—CH₂—CH—3—Py<br>  \|            \|<br>  CH₃      OH | Oil |
| 2-CH₂—CH=CH₂ | —C=CH—CO—3—Py<br>  \|<br>  CH₃ | M.p.: 92° C |
| 2-CH₂—CH=CH₂ | —CH—CH₂—CH—3—Py<br>  \|            \|<br>  CH₃      OH | Oil |
| 2,3-(OCH₃)₂ | —C=CH—CO—3—Py<br>  \|<br>  CH₃ | M.p.: 111° C |

-continued

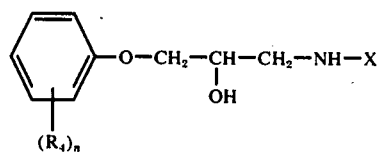

| $(R_4)_n$ | X | |
|---|---|---|
| 2,3-(OCH$_3$)$_2$ | —CH—CH$_2$—CH—3—Py<br>   \|         \|<br>   CH$_3$      OH | Oil |
| 2,6-Cl$_2$ | —C=CH—CO—3—Py<br>   \|<br>   CH$_3$ | M.p.: 118° C |
| 2,6-Cl$_2$ | —CH—CH$_2$—CH—3—Py<br>   \|         \|<br>   CH$_3$      OH | Oil |
| 2-Br | —C=CH—CO—3—Py<br>   \|<br>   CH$_3$ | M.p.: 129° C |
| 2-Br | —CH—CH$_2$—CH—3—Py<br>   \|         \|<br>   CH$_3$      OH | Oil |
| 4-OC$_3$H$_7$ | —C=CH—CO—3—Py<br>   \|<br>   CH$_3$ | M.p.: 100° C |
| 4-OC$_3$H$_7$ | —CH—CH$_2$—CH—3—Py<br>   \|         \|<br>   CH$_3$      OH | Oil |
| 4-Cl | —C=CH—CO—3—Py<br>   \|<br>   CH$_3$ | M.p.: 141° C |
| 4-Cl | —CH—CH$_2$—CH—3—Py<br>   \|         \|<br>   CH$_3$      OH | Oil |
| H | —C=CH—CO—3—Py<br>   \|<br>   CH$_3$ | M.p.: 93° C |
| H | —CH—CH$_2$—CH—3—Py<br>   \|         \|<br>   CH$_3$      OH | Oil |
| 4—O—CH(CH$_3$)$_2$ | —C=CH—CO—3—Py<br>   \|<br>   CH$_3$ | M.p.: 114° C |
| 4—O—CH(CH$_3$)$_2$ | —CH—CH$_2$—CH—3—Py<br>   \|         \|<br>   CH$_3$      OH | Oil |
| 4-OC$_8$H$_{17}$ | —C=CH—CO—3—Py<br>   \|<br>   CH$_3$ | M.p.: 108° C |
| 4-OC$_8$H$_{17}$ | —CH—CH$_2$—CH—3—Py<br>   \|         \|<br>   CH$_3$      OH | Oil |
| 4-Br | —C=CH—CO—3—Py<br>   \|<br>   CH$_3$ | M.p.: 157° C |
| 4-Br | —CH—CH$_2$—CH—3—Py<br>   \|         \|<br>   CH$_3$      OH | Oil |
| 2-C(CH$_3$)$_3$ | —C=CH—CO—3—Py<br>   \|<br>   CH$_3$ | M.p.: 139° C |
| 2-C(CH$_3$)$_3$ | —CH—CH$_2$—CH—3—Py<br>   \|         \|<br>   CH$_3$      OH | Oil |
| 3-N(CH$_3$)$_2$ | —C=CH—CO—3—Py<br>   \|<br>   CH$_3$ | M.p.: 117° C |
| 3-N(CH$_3$)$_2$ | —CH—CH$_2$—CH—3—Py<br>   \|         \|<br>   CH$_3$      OH | Oil |
| 2-cyclohexyl | —C=CH—CO—3—Py<br>   \|<br>   CH$_3$ | M.p.: 123° C |
| 2-cyclohexyl | —CH—CH$_2$—CH—3—Py<br>   \|         \|<br>   CH$_3$      OH | Oil |
| 2—O—CH$_2$—C≡CH | —C=CH—CO—3—Py<br>   \|<br>   CH$_3$ | M.p.: 116° C |

-continued

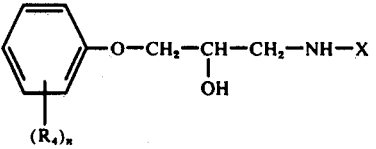

| $(R_4)_n$ | X | |
|---|---|---|
| 2—O—CH$_2$C≡CH | —CH—CH$_2$—CH—3—Py<br>  \|         \|<br>  CH$_3$    OH | Oil |
| 4—N(CH$_3$)—CO—C$_6$H$_5$ | —C=CH—CO—3—Py<br>  \|<br>  CH$_3$ | M.p.: 163° C |
| 4—N(CH$_3$)—CH$_2$—C$_6$H$_5$ | —CH—CH$_2$—CH—3—Py<br>  \|         \|<br>  CH$_3$    OH | Oil |
| 2,4-Br$_2$ | —C=CH—CO—3—Py<br>  \|<br>  CH$_3$ | M.p.: 127° C |
| 2,4-Br$_2$ | —CH—CH$_2$—CH—3—Py<br>  \|         \|<br>  CH$_3$    OH | Oil |
| 2-CH=CH$_2$ | —C=CH—CO—3—Py<br>  \|<br>  CH$_3$ | M.p.: 112° C |
| 2-CH=CH$_2$ | —CH—CH$_2$—CH—3—Py<br>  \|         \|<br>  CH$_3$    OH | Oil |
| 2,6-(OCH$_3$)$_2$ | —C=CH—CO—3—Py<br>  \|<br>  CH$_3$ | M.p.: 129° C |
| 2,6-(OCH$_3$)$_2$ | —CH—CH$_2$—CH—3—Py<br>  \|         \|<br>  CH$_3$    OH | Oil |
| 4-Cl, 2-NH—CO—CH$_3$ | —C=CH—CO—3—Py<br>  \|<br>  CH$_3$ | M.p.: 122° C |
| 4-Cl, 2-NH—CO—CH$_3$ | —CH—CH$_2$—CH—3—Py<br>  \|         \|<br>  CH$_3$    OH | Oil |
| 2,4,5-(CH$_3$)$_3$ | —C=CH—CO—3—Py<br>  \|<br>  CH$_3$ | M.p.: 136° C |
| 2,4,5-(CH$_3$)$_3$ | —CH—CH$_2$—CH—3—Py<br>  \|         \|<br>  CH$_3$    OH | Oil |
| 2-CH$_2$—CH=CH—CH$_3$ | —C=CH—CO—3—Py<br>  \|<br>  CH$_3$ | M.p.: 108° C |
| 2-CH$_2$—CH=CH—CH$_3$ | —CH—CH$_2$—CH—3—Py<br>  \|         \|<br>  CH$_3$    OH | Oil |
| 4-Cl, 5-CH$_3$, -2-iC$_3$H$_7$ | —C=CH—CO—3—Py<br>  \|<br>  CH$_3$ | M.p.: 147° C |
| 4-Cl, 5-CH$_3$, -2-iC$_3$H$_7$ | —CH—CH$_2$—CH—3—Py<br>  \|         \|<br>  CH$_3$    OH | Oil |
| 4-Br, 2-Cl | —C=CH—CO—3—Py<br>  \|<br>  CH$_3$ | M.p.: 131° C |
| 4-Br, 2-Cl | —CH—CH$_2$—CH—3—Py<br>  \|         \|<br>  CH$_3$    OH | Oil |
| 2—OCH(CH$_3$)—CH=CH$_2$ | —C=CH—CO—3—Py<br>  \|<br>  CH$_3$ | M.p.: 117° C |
| 2—OCH(CH$_3$)—CH=CH$_2$ | —C—CH$_2$—CH—3—Py<br>  \|         \|<br>  CH$_3$    OH | Oil |
| 2-cyclopentenyl | —C=CH—CO—3—Py<br>  \|<br>  CH$_3$ | M.p.: 123° C |
| 2-cyclopentenyl | —CH—CH$_2$—CH—3—Py<br>  \|         \|<br>  CH$_3$    OH | Oil |

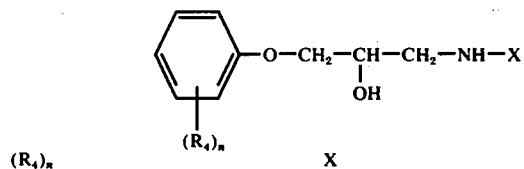

-3—Py denotes the radical—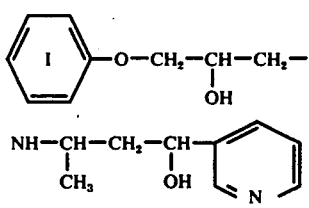

What we claim is:

1. Derivative of 1-phenoxy-3-amino-propane-2-ol having the structural formula in which the phenol nucleus I may be mono-, di- or tri-substituted by alkyl, alkenyl, alkinyl, cycloalkyl, cyclo-alkenyl, alkoxy, alkenyloxy, alkinyloxy, phenyl, halogen or the radical-$NR_1R_2$, in which $R_1$ stands for alkyl or acyl and $R_2$ stands for hydrogen or alkyl, their aldehyde condensation products, and their acid addition salts.

2. Derivative of 1-phenoxy-3-amino-propane-2-ol according to claim 1, wherein the phenyl nucleus I is mono-, di- or tri-substituted by alkyl containing 1 to 4 carbon atoms, alkenyl, or alkinyl each containing up to 6 carbon atoms, cycloalkyl or cycloalkenyl with a ring size of 5 to 8 carbon atoms in each case, alkoxy, alkenyloxy, or alkinyloxy containing up to 5 carbon atoms in each case, phenyl, chlorine, or bromine, or the radical —$NR_1R_2$, where $R_1$ stands for alkyl containing 1 to 4 carbon atoms or acyl containing up to 11 carbon atoms, and $R_2$ stands for hydrogen, or alkyl containing up to 4 carbon atoms.

3. Derivative of 1-phenoxy-3-amino-propane-2-ol according to claim 1, wherein the phenyl nucleus I is substituted by vinyl, allyl, metallyl, or crotyl.

4. Derivative of 1-phenoxy-3-amino-propane-2-ol according to claim 1, wherein the phenyl nucleus I is substituted by cyclopentenyl.

5. Derivative of 1-phenoxy-3-amino-propane-2-ol according to claim 1, wherein the phenyl nucleus I is substituted by cyclopentyl or cyclohexyl.

6. Derivative of 1-phenoxy-3-amino-propane-2-ol according to claim 1, wherein the phenyl nucleus I is substituted by methoxy, ethoxy, propoxy, butoxy, pentoxy, allyloxy, metallyloxy, or propargyloxy.

7. Derivative of 1-phenoxy-3-amino-propane-2-ol according to claim 1, wherein the phenyl nucleus I is substituted by the radical -$NR_1R_2$, in which $R_1$ stands for methyl, ethyl, acetyl, or benzoyl, and $R_2$ stands for hydrogen, methyl or ethyl.

8. Derivative of 1-phenoxy-3-amino-propane-2-ol according to claim 1, wherein the phenyl nucleus I is mono-substituted by methyl, phenyl, allyl, alkoxy with 1 to 5 carbon atoms, allyloxy, chloro, cyclopentyl, acetamino, or is di-substituted by chloro or methoxy, or is tri-substituted by methoxy.

9. 1-(3'-β-Pyridyl-3'-hydroxy-1'-methyl-propylamino)-3-(p-butoxy-phenoxy)-propan-2-ol, its aldehyde condensation products and said addition salts.

10. 1-(3'-β-Pyridyl-3'-hydroxy-1'-methyl-propylamino)-3-(p-butoxy-phenoxy)-propen-2-ol, its aldehyde condensation products and acid addition salts.

11. 1-(3'-β-Pyridyl-3'-hydroxy-1'-methyl-propylamino)-3-(m-methyl-phenoxy)-propan-2-ol, its aldehyde condensation products and acid addition salts.

12. 1-(3'-β-Pyridyl-3'-hydroxy-1'-methyl-propylamino)-3-(o-allyl-phenoxy)-propan-2-ol, its aldehyde condensation products and acid addition salts.

13. 1-(3'-β-Pyridyl-3'-hydroxy-1'-methyl-propylamino)-3-(p-propoxy-phenoxy)-propan-2-ol, its aldehyde condensation products and acid addition salts.

* * * * *